United States Patent [19]
Keown et al.

[11] Patent Number: 5,543,405
[45] Date of Patent: Aug. 6, 1996

[54] COMPOSITION AND METHOD FOR WEIGHT REDUCTION AND LONG TERM MANAGEMENT OF OBESITY

[76] Inventors: Wendy J. Keown, 8939 N. Camden Dr., Elk Grove, Calif. 95624; Betty J. Ford; Sandra L. Stoddard, both of 1250 Howe Ave., Sacramento, Calif. 95825

[21] Appl. No.: 326,750

[22] Filed: Oct. 20, 1994

Related U.S. Application Data

[63] Continuation of Ser. No. 142,496, Oct. 22, 1993, abandoned.

[51] Int. Cl.⁶ .................. A61K 31/555; A61K 31/62; A61K 31/605; A61K 31/60
[52] U.S. Cl. .................. 514/188; 514/161; 514/164; 514/165; 514/263; 514/653; 514/654; 514/910
[58] Field of Search .................. 514/188, 161, 514/164, 165, 653, 654, 263, 909, 910

[56] References Cited

U.S. PATENT DOCUMENTS 5,055,460  10/1991  Friedlander .................. 514/161
5,164,384  11/1992  Paul .................. 514/188

OTHER PUBLICATIONS

The Merck Manual, 14th edition (1982), Published by Merck Sharpe and Dohme, Rahway N.J., pp. 2340–2341.

*Primary Examiner*—Raymond Henley, III

[57] ABSTRACT

A weight reduction composition comprises a sympathomimetic agent and a mineral cation salt or chelate capable of enhancing carbohydrate metabolism, protein or fatty acid synthesis, retarding protein breakdown or lowering serum cholesterol levels such as trivalent and hexavalent chromium and vanadium salts and chelates. Preferred is a weight reduction composition containing ephedrine and chromium picolinate. This composition is presented in a variety of formulations, and is suitable for application to the reduction of weight of normal, slightly and grossly overweight humans.

14 Claims, No Drawings

COMPOSITION AND METHOD FOR WEIGHT REDUCTION AND LONG TERM MANAGEMENT OF OBESITY

CROSS-REFERENCE TO RELATED APPLICATIONS

This is a continuation of application Ser. No. 08/142,496, filed on Oct. 22, 1993 now abandoned.

BACKGROUND OF THE INVENTION

1. Field of the Invention

The present invention relates to the field of weight reduction and maintenance of body weight. More specifically, the present invention provides a composition that is particularly suited for the long term management of weight in general, and chronic obesity in particular, that is effective and lacks undesirable side effects produced by other known treatments.

2. Description of the Background

There is an ever increasing concern with personal weight and appearance. Diets and weight loss programs are extensively advertised that have varying degrees of effectiveness, and utilized by a large segment of Western society, even by persons with weights in the normal range. There is, therefore, a continuing search for new and effective means to facilitate weight loss.

Obesity, on the other hand is a real disease with consequences to the general health of a person. Originally presumed to result from simple overeating or the combination of overeating with inactivity, it is more and more being considered the result of a combination of a genetic predisposition with a poor diet and exercise habits. It has been suggested that the predisposition to obesity is associated with a defect in the sympathetic nervous system which manifests itself as a high efficiency in food intake. In normal persons, food intake results in a thermogenic response, that is, an increase in body metabolism in which the caloric content of the food is expended as heat. Some studies suggest that persons with a genetic predisposition to obesity are metabolically "more efficient" than lean persons, and store excess caloric energy as body fat. In obese persons, thermogenic defects may make a significant contribution to weight gain in the absence of a controlled food intake since calories which are not expended as heat are stored as excess weight.

Although there are concurrent opinions on the intense need for the treatment for obesity and its related disease processes, the role of medications being used for its treatment is controversial. In many chronic conditions such as hypertension, diabetes, heart disease, hyperlipidemia, etc., the absence of a "cure" for the misregulation by the organism is considered acceptable by the medical community. The irony is, of course, that while the relation of the exacerbation of these diseases by obesity is well documented, "intervention treatments" of these diseases are widely accepted by the medical community whereas the treatment of the disease of obesity is mostly overlooked.

In fact, obesity is clearly a clinical condition where the absence of medication to achieve a long term cure is unacceptable. The belief that short term interventions will cure a chronic condition has hampered the development of medications and methods for producing and maintaining weight loss. However, substantial research and development on medications for weight loss and control of body weight has occurred in the field of anorexia. The majority of these anorexiant agents have received a negative image due to their classification as schedule II, III and IV, and their potential for dependence and abuse.

In addition to this, it has been shown that a high resting metabolic rate (RMR) is associated with metabolically active tissues. Thus, the RMR, and therefore the total energy expenditure, can be expected to decrease as the body cell mass diminishes during a program of weight reduction. This is commonly known as a slowing of the metabolic rate in response to dieting, which results in a plateau in the dieter's weight after an initial period where weight loss occurs. A significant complication of weight loss is the loss of a high percentage of lean body mass (and the associated decrease in metabolic rate) as opposed to the loss of body fat. The rate of weight loss, in effect, decreases with time when an individual is adhering to a diet in which energy intake is reduced. This has been attributed to the decrease in the RMR (energy expenditure) that occurs when the energy intake is restricted and may be attributed to the following factors.

(1) Loss of lean body mass, which results in a decreased RMR.

(2) Lower thermogenic effect of food related to the lower energy intake.

This decrease in RMR, whether due to a genetic thermogenic defect or the consequence of a hypocaloric diet for weight loss, will produce the undesirable consequence of decreasing thermogenesis and the individual's caloric burning capacity.

It is evident that for obesity to occur, the energy intake must exceed the energy expended. Most pharmacological approaches to the treatment of obesity and methods of weight loss primarily focus on lowering the energy intake of the obese patient and resort to anorectic drugs that modify the metabolism of brain neurotransmitters involved in appetite regulation.

Various pharmaceutical compositions have been developed with the purpose of stimulating thermogenesis and thereby inducing weight loss. U.S. Pat. No. 5,019,594 provides a method of decreasing appetite by administering a composition containing ephedrine or other indirect acting sympathomimetic drugs and tyrosine or a tyrosine precursor. Ephedrine, an indirect sympathomimetic agent, is said to stimulate thermogenesis in laboratory animals, presumably by acting on their brown adipose tissue. In theory, the catecholamines activate thermogenesis in the brown adipose tissue of animals by binding to the animal's adrenergic receptors. Numerous studies have been published on the thermogenic response of humans and mammals to ephedrine treatment. The anorectic effect of ephedrine has also been investigated in rats. Ephedrine, however, used alone, was shown not to produce elevated blood pressure and tremors.

The thermogenic response elicited by ephedrine, methoxyphenamine, yohimbine, tranylcypromine, amitriptyline, iprindole and theophylline was studied in various mice and rat models, and found to differ with the respective drugs and the animal models used. For example, in mice made obese by a chemical lesion in the hypothalamus, all the drugs with the exception of theophylline caused a reduction in body fat without loss of body protein. All six drugs with the exception of theophylline caused a reduction in body fat without loss of body protein and produced a state of negative energy balance by means of a thermogenic effect. In contrast, in mice made obese by feeding a high protein, high fat diet, all seven drugs caused a negative energy imbalance. In genetically obese mice, only ephedrine and tranylcypromine were found to have any thermogenic activity. Similar variabilities in their physiological effects was seen in the rat models. The activity of thermogenic drugs in humans has been postulated to involve brown adipose tissue, as well. However, the proposed mechanism of action has never been verified in humans.

The affect of combinations of ephedrine with additional compounds such as caffeine, was also studied. In 1972, a composition containing ephedrine, caffeine and phenobarbital was noted as inducing loss of appetite and weight loss in humans. This composition, popularly known as the "Elsinore pill" was widely prescribed. However, serious side effects such as cutaneous reactions (tremors) were reported with this composition. Ephedrine/caffeine compositions without phenobarbital have also been investigated to reduce the side effects of the Elsinore pill. However, patients receiving this "modified Elsinore pill" continued to suffer from tremors similar to the effects seen with the Elsinore pill. More recent studies of the thermogenic effect in humans of a mixture of ephedrine and methylxanthines, such as caffeine and theophylline, have been reported by Dulloo and Miller (American J. Cain. Nutrition 43:388 (1986) and International J. Obesity 10:467 (1986)). These studies suggest that ephedrine/methylxanthine mixtures are more effective than ephedrine given alone. Methylxanthines are reported as potentiating the thermogenic anti-obesity effect of ephedrine and leading to normalization of body weight and body composition. However, other publications suggest that caffeine has no potentiating effect on the action of ephedrine. More recently, U.S. Pat. No. 5,055,460 disclosed the use of a composition containing caffeine, ephedrine and aspirin for weight reduction. The thermogenic effect of ephedrine/ethylephrine was reported to give inconclusive results. Aspirin, on the other hand, appears to potentiate the thermogenic effect of ephedrine.

Insulin is widely known to be one of the most powerful anabolic hormones in the body and the primary driver of amino acids and glucose into muscle cells. In muscle tissue, insulin initiates the transport of glucose, mineral ions and amino acids, and also regulates the synthesis and degradation of macromolecules. Insulin, in addition, decreases muscle catabolism during exercise which allows greater gains from intense exercise. It has been found that increased insulin activity affects tissues, and in particular muscle tissue, in a manner that promotes increased protein synthesis and muscle growth. Although insulin is primarily known for its ability to promote tissue uptake of blood sugar, i.e., glucose, it exerts a number of other important physiological effects, as well. These effects include increased synthesis and retention of protein in skeletal muscle and other tissues, stimulation of activated immune cells, enhanced brain uptake of tyrosine and tryptophan (precursors for important brain neurotransmitters), reduced output of free-fatty acids from adipose stores, accelerated potassium uptake by cells, and increased metabolic rate. Additionally, insulin mediates the thermogenic effect of carbohydrates which typically cause an increase in the metabolic rate following the absorption of dietary carbohydrates. Such mediation occurs through insulin activation of fat burning in "brown fat". Insulin is also required for proper thyroid function, and stimulates the "sodium pump", an enzyme that regulates ion movements and accounts for a significant fraction of the metabolic energy burned everyday. Studies have indicated a tendency for mature adults to lose sensitivity to insulin. A sedentary lifestyle, excess weight, and an over-refined diet (i.e., low fiber, low chromium, high in sugars) all contribute to a decreased insulin sensitivity. Studies have also found that individuals with impaired insulin sensitivity are at risk for high blood pressure, hypertension, heart disease and diabetes.

Numerous studies have found that vanadyl sulfate and chromium, when ingested, have properties that closely mimic as well as enhance many of the physiological effects of insulin. It has been found that these elements serve to both increase the effectiveness and enhance the anabolic effects of insulin. Supplementation of these elements into a normal diet has been shown to increase lean body mass without increasing body fat, stabilize blood sugar, i.e., glucose levels, increase the responsiveness of cells to insulin and lower blood fat levels. By their ability to potentiate the effects of insulin, both vanadyl sulfate and chromium have been found to enhance the entry of glucose (for energy) and amino acids (for protein synthesis) into muscle cells and inhibit the action of enzymes that catabolize the amino acids and proteins. It has further been found that these particular elements have cholesterol lowering, energy producing and anabolic promoting properties, which provide an optimal environment for anabolic development, weight/fat loss and energy output. Various cation salts have been tested for different applications. U.S. Pat. No. 4,315,927 discloses the formulation of essential metals as coordination complexes of picolinic acid, the pertinent portion of which is incorporated herein by reference. U.S. Pat. No. 5,013,752, on the other hand, proposes the administration of chromium picolinate in an edible food bar for the treatment of alcoholism. A mixture of chromium picolinate, chromium nicotinate glycinate, and vanadyl sulfate was disclosed in U.S. Pat. No. 5,164,384 as a dietary supplement for weight loss and cholesterol lowering.

The ideal drug for obesity was defined as being one that not only increases metabolic rate and causes loss of body fat but achieves these effects without a loss of body protein.

There is, therefore, a continuing search for new and more effective treatments to facilitate weight loss and for the treatment of long term management of obesity that lack the drawbacks of prior art treatments.

SUMMARY OF THE INVENTION

The present invention relates to a weight reduction composition which produces significant weight reduction over a period of time and is safe lacking the disadvantages of other prior art treatments. The weight loss composition of this invention can be administered both in conjunction with caloric restriction (diet) and in the absence of caloric restriction.

The composition of this invention comprises a sympathomimetic agent selected from the group consisting of phenylpropanolamine, ephedrine, methoxyphenamine, yohimbine, tyrosine, dopamine, caffeine, theobromine, papaverine, tranylcypromine, amitriptyline, iprindole, theophylline, amphetamine, pseudoephedrine, norpseudoephedrine, diethylpropion, benzphetamine, phendimetrazine, phenmetrazine, phentermine, chorphentermine, aminorex, and mixtures thereof, and a mineral cation salt or chelate selected from the group consisting of trivalent and hexavalent chromium, and vanadium.

The invention also provides a method for reducing weight and maintaining weight loss, which is achieved by administering the weight loss composition of the invention, optionally in conjunction with a caloric restriction program. The present invention is particularly well suited for long term programs which permit the patient to maintain a healthy diet but to have a reduced appetite without any undesirable side effects.

Other objects, advantages and features of the present invention will become apparent to those skilled in the art from the following discussion.

DESCRIPTION OF THE PREFERRED EMBODIMENTS

This invention arose from a desire by the inventors to provide a novel composition having superior characteristics over the currently utilized treatments for weight reduction in slightly overweight persons and obesity. The present inventors are providing a composition that promotes and maintains energy expenditure while at the same time sparing protein and reducing fat. Sympathomimetic agents such as ephedrine and others have been shown to have effective thermogenic properties, i.e., increasing energy expenditure, while having protein sparing effects that stimulate protein accumulation without affecting muscle protein breakdown, and also inducing the loss of body fat.

When a sympathomimetic agent is combined with a salt or chelate of a mineral cation such as chromium or vanadium, its protein/lean body mass sparing effect is dramatically potentiated along with an increase in the utilization of body fat by the increased thermic energy elicited. Importantly, the two types of compounds present in the composition of the invention work together synergistically to provide a medicinal product suitable for producing weight loss by enhancing the specific burning of body fat and increasing the expenditure of energy while retarding protein breakdown, increasing lean body mass and muscle development, providing an anorectic effect and normalizing insulin levels in blood. The present invention has been shown to have an excellent effect for the reduction of weight and to be suitable for prolonged use and can therefore be utilized for the long term management of obesity.

In addition, the composition of the present invention is also useful for inducing weight reduction in humans of relatively normal weight, where additional weight loss or plain weight maintenance is desirable. Thus, a segment of the population which in general weighs between five and twenty pounds more than what is considered a normal weight for their height may also benefit from the present treatment.

Thus, the inventors are hereby providing a weight reduction composition that comprises a sympathomimetic agent such as ephedrine, methoxyphenamine, yohimbine, tyrosine, dopamine, caffeine, theobromine, papaverine, tranylcypromine, amitriptyline, iprindole, theophylline, amphetamine, phenylpropanolamine, pseudoephedrine, norpseudoephedrine, diethylpropion, benzphetamine, phendimetrazine, phenmetrazine, phentermine, chorphentermine, aminorex, or mixtures thereof, and a mineral cation salt or chelate capable of enhancing carbohydrate metabolism, protein or fatty acid synthesis, retarding protein breakdown or lowering serum cholesterol levels, such as trivalent and hexavalent chromium and vanadium salts and chelates in an absorbable form. The chromium ion may be present as chromium picolinate, chromium nicotinate glycinate or chromium polynicotinate. However, other mineral salts or chelates of these cations are also suitable as long as they can be absorbed by the human body. Preferred are salts or chelates of trivalent chromium, and more preferred is chromium picolinate.

Among the sympathomimetic agents, preferred, is ephedrine, and the most preferred form of the present invention is a weight loss composition that comprises both ephedrine and chromium picolinate.

In addition to these two components, the weight loss composition of the invention may further comprise a carrier or diluent. Carriers or diluents suitable for use herein must be pharmaceutically-acceptable and are generally known in the field. The components of the present composition may be admixed as is known in the art and formulated in accordance with standard procedures. Exemplary pharmaceutically-acceptable forms of formulations for the weight loss composition include solid, crystalline, microcrystalline, particles, pellets, granules, powder, tablets, spray-dried, lyophilized, and the like, forms that may dissolve or undergo disintegration and dissolution in the presence of a parenteral fluid including intravenous fluids, compressed forms that undergo disintegration and dissolution in the presence of fluids such as compressed agents, compressed powders, compressed granules, friable layers of agents, and the like, and other formulations such as dragees, capsules, as well as injectable, transdermal, inhalable, implantable, and other forms known in the art such as suppositories, including vaginal and rectal suppositories, patches, and implants that are known in the art. The composition may be provided in solid, liquid or other forms that are suitable for administration to humans. In addition to the sympathomimetic agent, the salt or chelate and the carrier or diluent, the present composition may further comprise other ingredients such as electrolytes, buffers, colorants, compounding agents, aromatic agents, bulking agents, formulation agents, binders, dispersants, wetting agents, suspending agents, lubricants and dyes. Representative of these include suspending agents such as acacia, agar, calcium carrageenan, alginic acid, algin, agarose powder, collagen, colloidal magnesium silicate, colloidal silicon dioxide, hydroxyethyl cellulose, pectin, gelatin and calcium silicate, binders like polyvinyl pyrrolidone, and magnesium stearate, wetting agents such as fatty amines, fatty quaternary ammonium salts, and the like. Drug formulation indicates in the present context that the drugs are present in the compartment accompanied by other components, such as an osmagent, a binder, dye and the like, all of which must be pharmaceutically-acceptable and well tolerated by the human body. The term formulation, and the expression formulation agents is used herein, and, generically indicates that the composition of the invention is formulated, mixed, added, dissolved, suspended, solubilized, formulated into a solution, solid mixture, and the like, for the purpose of oral, systemic, parenteral, or transdermal administration. The oral route is the most commonly used one for the self administration of medicines by a patient. The transdermal route of delivery of drugs provides many advantages, and transdermal systems for the delivery of drugs and other agents are described, for example, in U.S. Pat. Nos. 3,598,122; 3,598,123; 4,379,454; 4,286,593; 4,314,557 and 4,568,343, among others, the pertinent portions of which are incorporated herein by reference.

Conventional dosage forms, such as tablets or injections can serve to administer the combination of two or more of the present active agents, each at its appropriate dose, merely by the appropriate selection of the amount of each agent included in the dosage form.

In transdermal delivery devices, however, the total dosage of each agent is not established by the amounts of each agent that are in the device. Instead, the total dosage is a product of its average transdermal administration rate (µg/hr) and the time over which the device is applied, and the average administration rate of an agent from a transdermal delivery device is determined primarily by a combination of factors other than the amount of the agent present in the device. When two or more agents present in a composition have different dermal permeabilities, it may be preferable to deliver them from two separate reservoirs rather than from a common one. This is particularly the case when the dosage of the two, as in the present case, may differ. Permeation enhancers may also be utilized to increase the inherent permeability of the skin to one or more of the agents being delivered. Before the transdermal administration of an agent into the blood stream can commence at a steady state rate, the capacity of the skin below the device to bind each agent present in the composition must be saturated. The time required to achieve the steady state rate is known as the lag time, and is a function of the rate at which the agent permeates into the skin and the binding capacity of the skin for that agent. In order to achieve, orally or by injection, a particularly uniform, variable or modulated, blood level of the drugs in the present composition, it may be necessary to administer multiple unit doses over a 24 hr. period. Neither of these modes of administration, however, achieves the blood level of the two drugs in circulation to remain constant. It is extremely difficult, if not impossible, to achieve a constant blood level of a drug in circulation when it is administered orally, except when utilizing sustained release formulations. This is true even though the drug is administered at periodic intervals according to a well defined schedule. One reason for this is that the rate of absorption of drugs through the gastrointestinal tract is affected by the contents of the tract. Such variables as whether the drug is administered before or after eating and the type and quantity of food eaten (for example, its high or low fat content) or administered before of after a bowel movement, can control the rate of absorption of the drug in the gastrointestinal tract. As most of the absorption of drugs takes place in the small intestine, the time of passage through the small intestine is another governing factor. This, in turn, is also affected by the rate of the intestine's peristaltic contractions. Also important is the rate of circulation of the blood to the small intestine.

The almost inevitable result of the oral administration of drugs through the gastrointestinal tract is a surge in the level of drug in circulation surges each time the drug is administered, followed by a decline in its concentration in the blood and body compartments. Thus, a plot of the level of a drug in circulation the administration of several tablets a day has the appearance of a series of peaks, some of which may surpass the toxic threshold, and valleys. Clearly, when the blood level decreases below a critical point needed to achieve the desired therapeutic effect, that effect will no longer be attained.

The administration of the composition by injection is inconvenient, painful, and poses a risk of local tissue reaction and infection. Moreover, the typical result of the administration of a drug by injection is a surge in the concentration of the drug in serum immediately after injection, followed by a decline and another surge in concentration upon each subsequent injection.

Other dosage forms such as rectal suppositories and sublingual lozenges are also suitable but produce non-uniform levels of the therapeutic agents in circulation. These dosage forms require great patient cooperation, have low patient acceptability, and are sparingly used throughout most of the world.

The dosage forms described above bring about a pulse entry of drugs, that is, a concentrated dose of drug is brought into contact with an organ of entry at a particular time unit. Undoubtedly, this creates drug concentrations beyond the capacity of the active centers to accept (that is, the saturation point may be exceeded by many orders of magnitude) and, also, until dilution in body fluids takes place the capacity of metabolic and excretory mechanisms may be exceeded. The result is that a toxic level of the drug(s) is (are) allowed to build for a period of time, with detrimental effects to particular tissues or organs. To obtain persistence of effect, the usual approach is to make the initial dose high or to modify the drug structure to obtain a longer metabolic half-life of the drug in circulation. Raising the initial dosage may worsen the problem. Many derivatives with long half-lives have a lower therapeutic index (ratio of the median toxic dose to the median effective dose) than that of the parent compounds, and these approaches, therefore, are not the answer to the problem.

The present composition may be administered through the skin. Percutaneous administration can have the advantage of permitting the continuous administration of the drugs to the circulation over a prolonged period of time to attain a uniform delivery rate and blood level of the drugs. The commencement and termination of drug therapy are attained by the application and removal from the skin of the dosing devices. The uncertainties associated with the administration through the gastrointestinal tract and the inconvenience of administration by injection are eliminated. Since a high concentration of drug never enters the body when given by percutaneous administration, any problems associated with pulse entry are overcome and the metabolic half-life of the drug is not a factor of controlling importance.

Another approach to the problem of alternatively high and low levels of a drug in blood are sustained release or time capsules in oral dosage form. This is a particularly preferred mode of formulation for the present composition. Sustained release forms can be made in many embodiments, including those that release the present agents into the gastrointestinal tract over time. Sustained release systems for oral administration may have various conventional shapes and sizes such as round with various diameters, or they can be shaped like a capsule having a range of sizes from 000 to 0, and from 1 to 8. The sustained release embodiment of the composition of the invention may also be designed as an osmotic device designed for placement in a body passage way such as the vagina or the anal-rectal canal. In either case, it may have an elongated, cylindrical, self-sustaining shape, e.g., with a rounded lead end and a trailing end, and it may be equipped with a manually controlled means for easy removal. These sustained release formulations may be manufactured with a wall formed of a material that does not adversely affect the sympathomimetic agent and the cation salt or chelate present in the composition. The selectively, semi-permeable materials forming the wall of the sustained release dosage form are insoluble in fluids and they may be erodible, for short term use, or non-erodible for long term use. Typical materials for forming the walls of the sustained release formulations include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminoacetate, cellulose acetate ethyl carbamate, cellulose acetate chloroacetate, cellulose dipalmatate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the co-precipitation of a polyanion and a polycation as disclosed, for example, in U.S. Pat. Nos. 3,173,867; 3,276,586; 3,541,005; 3,541,006; and 3,546,142, semipermeable polymers as disclosed, for instance, in U.S. Pat. No. 3,133,132, lightly cross-linked polystyrene derivatives, cross-linked poly(-sodium styrene sulfonate), poly(vinylbenzyltrimethyl ammonium chloride), cellulose acetate having a degree of substitution of up to 1 and an acetyl content of up to 21%, cellulose diacetates having a degree of substitution of 1 to 2 and an acetyl content of 21 to 35% cellulose triacetate having a degree of substitution of 2 to 3 and an acetyl content of 35 to 44.8% as disclosed, for example, in U.S. Pat. No. 4,160,020.

In another embodiment of the sustained release formulation of the composition of the invention may be in the form of a hydrogel which is made from swellable hydrophilic polymers. The swellable, hydrophilic polymers are in one preferred embodiment lightly cross-linked, with the cross-links, e.g., being formed by covalent or ionic bonds which interact with water and aqueous biological fluids and swell or expand to some equilibrium state. The hydrogels exhibit the ability to swell in water and retain a significant fraction of water within its structure, and when cross-linked they will not dissolve in the water. The hydrogels can be of plant and animal origin, hydrogels prepared by modifying naturally occurring structures, and synthetic polymer hydrogels, among others. The polymers swell or expand to a very high degree, usually exhibiting a 2 to 50 fold volume increase. Hydrophilic polymeric materials for the purpose include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable co-polymer produced by forming a dispersion of finely divided co-polymers of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other hydrogels include hydrogels exhibiting a cross-linking of 0.05 to 60% hydrophilic hydrogels known as Carbopol® acidic carboxy polymer, Cyanamer® polyacrylamides, cross-linked water-swellable indenemaleic anhydride polymers, Good-rite® polyacrylic acid, polyethyleneoxide, starch graff copolymers, Aqua-Keeps® acrylate polymer, diester cross-linked polyglucan, and the like. The hydrogels are exemplified in U.S. Pat. No. 3,865,108 issued to Hartop; 4,207,839 issued to Manning; in U.S. Pat. No. 4,207,893 issued to Michaels; and Handbook of Common Polymers, by Scott and Roff, Chemical Rubber Company, Publisher, Cleveland, Ohio. Included as different embodiments of the present formulation are pessaries, prosthesis, insertable bullets, eliptical, circular, bulbous, loops, bows, or any other geometrical shape that readily lends itself to intrauterine and anal placement as exemplified in U.S. Pat. Nos. 3,319,625; 3,256,878; 3,397,691; 3,323,520; 3,405,711; and 3,077,879, among others.

The present composition may comprise a broad range of percentages of the components of the invention. The sympathomimetic agent may be present in an amount of about 0.001 to 99.9 wt %, and the mineral cation salt or chelate may be present in an amount of about 0.0001 to 99.99 wt %. When other components are also present, such as a carrier and others mentioned above, they are compounded with the two or more drugs present in the composition and they are present in standard amounts. Preferred amounts of the sympathomimetic agent are about 0.1 to 25 wt %, and of the mineral cation salt or chelate about 0.001 to 2.5 wt %. Other amounts, however, are also suitable. In one preferred embodiment, the composition of the invention is formulated in bulk, and may be sold for their own dispensation to, e.g., pharmacies and dietary clinics. In another embodiment, the composition of the invention is formulated in unit dosage form for self-administration by a patient, and it may be sold in quantities sufficient for one week, one month, two months, six months, one year, or longer periods. The transdermal formulation may contain sufficient amounts of the two components for delivery for periods of about one month to three months, and even longer periods. In one preferred embodiment, the unit dosage form contains, for instance, about 1 to 1000 mg sympathomimetic drug and about 1 to 2,000 mcg chelate or salt, and more preferably about 25 to 350 mg sympathomimetic agent, and about 100 to 1,000 mcg of salt or chelate. Other amounts, however, are also suitable, and preferred are about 50 to 250 mg sympathomimetic agent, e.g., ephedrine, and about 100 to 250 mcg salt or chelate, e.g., chromium picolinate. In a still more preferred embodiment, the sustained release form comprises about 25 to 350 mg ephedrine and about 100 to 1,000 mcg chromium picolinate. Similar amounts of the other sympathomimetic agents and salts or chelates are also suitably present. The composition of the invention may also comprise other agents that are suitable for aiding in weight reduction, such as acetylsalicylic acid, in a preferred amount of about 1 to 2,000 mg, and more preferred about 5 to 500 mg. In a particularly preferred embodiment of the invention, the weight loss composition comprises about 25 to 350 mg ephedrine, about 100 to 1,000 mcg chromium picolinate, and about 5 to 500 mg acetylsalicylic acid.

As already indicated, the composition of the invention may be applied to the fostering of weight reduction by limiting the caloric intake of a patient to a value less than the caloric expenditure of the subject, and jointly administering to the subject a weight reduction aiding amount of the present composition until a predetermined weight reduction is attained. The composition of the invention may be administered daily, several times a day, or in the case of a sustained release formulation once a day, once a week, once a month, and the like. Once a predetermined weight is attained, the patient may be administered a weight maintenance effective amount of the composition by itself, or while continuing to limit caloric intake. The present treatment is particularly suitable for long term use, since it neither brings about undesirable side effects nor does it lose its effectiveness over time. The administration of the present composition may be conducted by itself or by also limiting the caloric intake of the patient, since it, by itself, has an appetite limiting effect.

Having now generally described this invention, the same will be better understood by reference to certain specific examples, which are included herein for purposes of illustration only and are not intended to be limiting of the invention or any embodiment thereof, unless so specified.

EXAMPLES

Example 1: Set-up for the Clinical Trials

The different treatments were administered in a clinical trial involving 30 healthy but obese (overweight? ) women. The trial was conducted over a period of eight weeks, and the population was divided into five groups of six women each. All groups were maintained on a similar controlled hypocaloric diet consisting of three meals a day incorporating protein, carbohydrates (high fiber), fats, restricted sugar, restricted sodium, and restricted fat. The patients were instructed to eat within the prescribed diet regimen take medication as directed, and required to be evaluated once a week for weigh-in, blood pressure, diet and review. The average age of the participants was 42½ yrs, and the groups were comparable in their composition and ages. Each patient was under the strict supervision of a physician, and was monitored by either a registered nurse (RN) or a licensed vocational nurse (LVN). Each patient was accepted into the trial, given an initial physical exam and her medical history was taken. Blood was drawn in a fasting state and utilized for a full chemistry panel, complete blood count (CBC), and full urinalysis. The patients in all groups were monitored weekly. At the time of each visit the patient's weight, body measurements and blood pressure were taken, the diet & results reviewed, medicine for the coming week dispensed with specific instructions for its use. Overall, none of the treatments appeared to have an effect on the blood pressure of the patients. All comments relating to reactions and side effects of each patient were noted on the patient's chart at the time of their weekly visit.

The five groups and the medication given the patients in each group were as follows.

Group 1: Hypocaloric diet and a total daily dose of 200 mcg chromium picolinate.

Group 2:. Hypocaloric diet and a total daily dose of 75 mg phenylpropanolamine.

Group 3: Hypocaloric diet and a total daily dose of 75 mg ephedrine alone.

Group 4: Hypocaloric diet and a total daily dose of 75 mg ephedrine and 200 mcg chromium picolinate.

Group 5: Hypocaloric diet and a total daily dose of 75 mg ephedrine and 325 mg acetylsalicylic acid,

Example 2: Administration of Chromium Salt Alone with Hypocaloric Diet (Group 1)

Each patient was instructed to take one tablet of chromium salt twice daily, once at 11 am and once at 4 pm. Each tablet contained 100 mcg of the medication. Each patient's weekly weight was recorded, and her total weight loss at the end of an eight week period calculated from the first and last measurements. The average weight loss for the group was calculated from these figures, and all results are shown in Table 1 below.

TABLE 1

Weekly Weights of Patients on Hypocaloric Diet plus Chromium Salt ( Group 1 )

| Patient | Total Loss | 1 | 2 | 3 | 4 | 5 (lbs) | 6 | 7 | 8 |
|---|---|---|---|---|---|---|---|---|---|
| CL | 5.50 | 149.50 | 144.50 | 147.00 | 148.50 | 145.00 | 145.00 | 144.50 | 144.00 |
| JG | −8.75 | 192.25 | 189.25 | 186.25 | 196.00 | 188.50 | 194.75 | 201.25 | 200.00 |
| GG | 3.25 | 150.25 | 149.50 | 147.50 | 145.50 | 145.50 | 146.25 | 146.25 | 147.00 |
| EV | 2.00 | 159.50 | 157.00 | 159.75 | 159.50 | 157.50 | 156.00 | 157.00 | 157.50 |
| PD | 2.00 | 153.00 | 149.75 | 153.25 | 147.25 | 147.75 | 146.00 | 146.00 | 157.50 |
| LH | 13.00 | 210.00 | 201.00 | 201.50 | 200.00 | 198.00 | 200.00 | 198.50 | 197.00 |
| Ave. | 5.75 | | | | | | | | |

Example 3: Administration of Phenylpropanolamine Alone with Hypocaloric Diet (Group 2)

All patients in this group were given their medicine weekly during their visit to the clinic, and were advised to take the extended release tablets of the medicine at 11 am every day. Their weekly weights, total weight loss at the end of eight weeks and the average weight loss for the group are shown in Table 2 below.

TABLE 2

Weekly Weights of Patients on Hypocaloric Diet plus Phenylpropanolamine ( Group 2 )

| Patient | Total Loss | 1 | 2 | 3 | 4 | 5 (lbs) | 6 | 7 | 8 |
|---|---|---|---|---|---|---|---|---|---|
| CW | 11.00 | 179.50 | 175.00 | 171.50 | 169.25 | 168.50 | 167.50 | 167.25 | 168.50 |
| JR | 7.50 | 161.50 | 158.50 | 158.50 | 158.00 | 156.00 | 154.75 | 154.25 | 154.00 |
| MD | 11.50 | 158.75 | 153.00 | 151.25 | 150.50 | 150.00 | 150.00 | 149.50 | 147.25 |
| BH | 2.50 | 154.00 | 153.50 | 152.50 | 151.00 | 150.00 | 150.25 | 148.50 | 151.50 |
| PT | 8.00 | 123.25 | 120.75 | 118.50 | 118.50 | 115.00 | 116.25 | 116.25 | 115.25 |

TABLE 2-continued

Weekly Weights of Patients on Hypocaloric Diet plus Phenylpropanolamine (Group 2)

| Patient | Total Loss | Week 1 | 2 | 3 | 4 | 5 (lbs) | 6 | 7 | 8 |
|---|---|---|---|---|---|---|---|---|---|
| DN | 12.00 | 228.00 | 225.00 | 228.75 | 221.25 | 217.00 | 224.00 | 216.50 | 216.00 |
| Ave. | 8.75 | | | | | | | | |

Example 4: Administration of Ephedrine Alone with Hypocaloric Diet (Group 3)

Each patient was instructed to take one tablet of ephedrine (25 mg each) three times a day one-half hour before each meal. The weekly variation of each patient's weight, the total weight loss over a period of eight weeks and the average weight loss for the group are shown in Table 3 below.

TABLE 3

Administration of Ephedrine Alone with Hypocaloric Diet (Group 3)

| Patient | Total Loss | Weeks 1 | 2 | 3 | 4 | 5 (lbs) | 6 | 7 | 8 |
|---|---|---|---|---|---|---|---|---|---|
| LB | 16.50 | 164.75 | 159.50 | 156.25 | 154.00 | 153.50 | 152.00 | 150.00 | 148.50 |
| CB | 14.50 | 203.25 | 198.50 | 194.25 | 192.50 | 190.50 | 188.25 | 189.00 | 188.75 |
| CJ | 18.00 | 163.50 | 160.25 | 156.50 | 154.00 | 153.25 | 148.25 | 147.00 | 145.50 |
| JA | 18.25 | 181.50 | 177.50 | 175.75 | 173.00 | 171.00 | 168.75 | 167.00 | 163.25 |
| DH | 18.75 | 202.75 | 199.50 | 195.25 | 191.25 | 188.50 | 186.50 | 184.25 | 184.00 |
| JK | 16.25 | 162.75 | 160.00 | 157.00 | 151.50 | 150.75 | 148.50 | 147.00 | 146.50 |
| Ave. | 17.25 | | | | | | | | |

Example 5: Combined Administration of Ephedrine and Chromium Salt and Hypocaloric Diet (Group 4)

Each patient was instructed to take one chromium tablet (100 mcg) twice a day at 11 am and 4 pm and one ephedrine tablet (25 mg each) three times a day one hour before each meal. The weekly weight, total weight loss per patient and the average loss for the group are shown in Table 4 below.

TABLE 4

Weekly Weights of Patients on Combined Ephedrine and Chromium plus Hypocaloric Diet (Group 4)

| Patient | Total Loss | Weeks 1 | 2 | 3 | 4 | 5 (lbs) | 6 | 7 | 8 |
|---|---|---|---|---|---|---|---|---|---|
| MP | 22.25 | 221.75 | 218.75 | 214.00 | 212.50 | 207.00 | 203.00 | 201.75 | 199.50 |
| RS | 27.50 | 175.50 | 166.00 | 161.00 | 156.00 | 156.50 | 152.50 | 148.75 | 148.00 |
| DT | 19.00 | 151.00 | 145.75 | 142.75 | 138.75 | 136.50 | 133.75 | 133.25 | 132.00 |
| DR | 20.50 | 194.50 | 189.25 | 185.00 | 183.00 | 180.00 | 177.00 | 174.25 | 174.00 |
| AF | 21.00 | 241.00 | 238.25 | 233.00 | 230.00 | 225.50 | 222.50 | 220.50 | 220.00 |
| AD | 22.25 | 197.25 | 194.75 | 191.00 | 187.50 | 184.25 | 180.00 | 175.50 | 175.00 |
| Ave. | 22.25 | | | | | | | | |

Example 6: Combined Administration of Ephedrine and Acetylsalicylic Acid with Hypocaloric Diet (Group 5)

Each patient was instructed to take one tablet of ephedrine (25 mg each) three times a day one hour before each meal and one tablet of acetylsalicylic acid (325 mg) once a day. The weekly weights of the patients, their total weight loss over a period of eight weeks and the average weight loss for the group are shown in Table 5 below.

TABLE 5

Weekly Weights of Patients on Ephedrine and Acetylsalicylic Acid plus Hypocaloric Diet (Group 5)

| Patient | Total Loss | 1 | 2 | 3 | 4 (lbs) | 5 | 6 | 7 | 8 |
|---|---|---|---|---|---|---|---|---|---|
| CH | 11.00 | 167.00 | 162.00 | 161.00 | 160.50 | 159.00 | 158.50 | 157.00 | 156.00 |
| DR | 10.50 | 201.25 | 198.00 | 197.50 | 196.00 | 194.50 | 193.00 | 192.25 | 190.00 |
| SJ | 13.00 | 163.00 | 160.00 | 158.00 | 156.50 | 154.00 | 153.00 | 151.00 | 150.00 |
| BH | 8.00 | 181.25 | 180.00 | 179.50 | 178.25 | 177.00 | 175.50 | 174.25 | 173.25 |
| JR | 10.00 | 201.50 | 199.00 | 197.50 | 196.00 | 195.50 | 194.00 | 193.00 | 191.50 |
| LD | 12.00 | 163.00 | 161.00 | 158.25 | 157.00 | 156.50 | 154.00 | 153.00 | 151.00 |
| Ave. | 10.75 | | | | | | | | |

Example 7: Results

All patients were subjected to a similar hypocaloric diet consisting of three meals a day as described in Example 1 above. In addition, each patient self-administered the medicines as described in Examples 1 to 6 above.

The total weight loss for all patients in Group 1 administered the chromium salt alone over a period of eight weeks was 39.50 lbs. An average weight loss per patient of 5.75 lbs was obtained for this treatment over a period of eight weeks. No significant complaints or side effects were noted throughout the eight week period.

The total loss of weight over a period of eight weeks for all patients in Group 2 administered phenylpropanolamine alone was 52.50 lbs. An average 8.75 lbs per patient were lost during the trial. This group recorded complaints relating to the medication the patients were receiving, such as nervousness, restlessness, and rapid pulse. Two of the patients had an increase in pulse rate the first day the medicine was administered. The increase, however, was well tolerated and subsided after two doses of the medicine were administered. No increase in blood pressure was noted for any of the patients in the group. After three weeks of the treatment, complaints were noted in relation to the medicine losing its effect on appetite suppression. No other significant comments were noted.

The total weight loss for all patients in Group 3 administered ephedrine alone over a period of eight weeks was 102.25 lbs. No initial complaints by the patients were noted. No changes in blood pressure were noted either. Five of the patients noted a significant reduction in their appetite. An average 17.50 lbs per patient were lost with this treatment during the eight weeks.

The total loss of weight for all patients in Group 4 administered ephedrine and a chromium salt over a period of eight weeks was 132.50 lbs. On the average, each patient lost about 22.25 lbs during the eight week period. Neither initial complaints nor changes in blood pressure were noted for this group. All patients reported a significant decrease in appetite during the period that they were taking the medication.

The total weight loss for all patients in Group 5 administered ephedrine and acetylsalicylic acid over a period of eight weeks was 64.50 lbs. An average of 10.75 lbs per patient were lost with this medication over the time of the trial. Neither initial complaints nor changes in the blood pressure of the patients were noted. All patients reported a significant loss of appetite with this treatment. A summary of the results obtained for the various groups administered different medicines is shown in Table 6 below.

TABLE 6

Results Obtained with Different Treatments

| Group | 1 | 2 | 3 | 4 | 5 |
|---|---|---|---|---|---|
| Group Loss (lbs) | 39.50 | 52.50 | 102.25 | 132.50 | 64.50 |
| Loss per Patient (lbs) | 5.75 | 8.75 | 17.25 | 22.25 | 10.75 |

Example 7: Comments and Conclusions

A cursory comparison of the results obtained with the five different treatments tested clearly shows the unexpected superiority of the combined sympathomimetic agent/mineral cation salt therapy for the treatment of obesity. The weight loss by the group of patients receiving this combined treatment far surpassed any and all the other groups. It should be noted that once some weight loss is attained it becomes more difficult for the patient to continue to lose more weight because of the adaptation process that the patient's body goes through. Similarly, when a certain rate of weight loss is attained with the administration of one medicine, the addition of another will not necessarily add onto, let alone potentiate, the effect noted with the first treatment. In fact, this is the case when acetylsalicylic acid is added to the ephedrine treatment received by the patients of Group 5. No clear potentiation of the weight loss is seen. In this context, therefore, it is notable the far more effective action shown on this clinical trial by the combination therapy of a sympathomimetic agent such as ephedrine, and a mineral cation salt or chelate such as chromium picolinate.

The utilization of ephedrine and acetylsalicylic acid (with caffeine for weight reduction is disclosed in U.S. Pat. No. 5,055,460, the utilization of a mixture of chromium and vanadyl salts for weight reduction is disclosed in U.S. Pat. No. 5,164,384, and phenylpropanolamine (PPA) is the most popular over-the-counter drug selling in the US for appetite suppression today that has well known detrimental side effects. The effect of the present invention has, therefore, been shown to be unexpectedly superior to the effect of each one of its components alone and to treatments for weight reduction considered to be the closest in the art.

The invention now being fully described, it will be apparent to one of ordinary skill in the art that many changes and modifications can be made thereto without departing from the spirit or scope of the invention as set forth herein.

What is claimed as novel and desired to be patented by Letters Patent of the United States is:

1. A weight reduction composition, comprising from 25 to 75 mg. of ephedrine; and from 100 to 200 mcg. of a cation or chelate of chromium.

2. The composition of claim 1, wherein the chromium is present as chromium picolinate, chromium nicotinate glycinate or chromium polynicotinate.

3. The composition of claim 2, wherein said chelate comprises chromium picolinate.

4. The composition of claim 1, wherein said cation in comprises trivalent chromium.

5. The composition of claim 1, in unit dosage form.

6. The composition of claim 5, in sustained release form.

7. The composition of claim 6, in the form of a patch, implant, suppository, pessary, or an oral formulation.

8. The composition of claim 1, further comprising a pharmaceutically-acceptable carrier or diluent.

9. The composition of claim 1, further comprising an agent selected from the group consisting of electrolytes, buffers, colorants, aromatic agents, flavoring agents, emulsifying agents, compounding agents, formulation agents, permeation enhancers, other weight reduction agents, and bulking agents.

10. The composition of claim 1, further comprising an agent that is acetylsalicylic acid or selected from a sympathomimetic group consisting of phenylpropanolamine, methoxyphenamine, yohimbine, tyrosine, dopamine, caffeine, theobromine, papaverine, tranylcypromine, amitriptyline, iprindole, theophylline, amphetamine, pseudoephedrine, norpseudoephedrine, diethylpropion, benzphetamine, phendimetrazine, phenmetrazine, phentermine, chorphentermine, aminorex, and mixtures thereof.

11. The composition of claim 10, wherein the acetylsalicylic acid is present in an amount of about 1 to 3,000 mg.

12. A method of treatment for fostering weight reduction comprising administering to a subject in need of the treatment and on a hypocaloric diet an efficacious amount of a weight reducing composition, comprising:

a) ephedrine in a total daily dosage amount of 75 mg. and b) a cationic salt or chelate of chromium in a total daily dosage amount of 200 mcg.

13. The method of claim 12 wherein the hypocaloric diet comprises limiting the daily caloric intake of the subject to a value less than about the estimated caloric expenditure of the subject.

14. The method of claim 13, further comprising after a predetermined weight is attained, administering to the subject a weight maintaining effective amount of the composition.

* * * * *